United States Patent
Okano et al.

(10) Patent No.: US 7,863,059 B2
(45) Date of Patent: Jan. 4, 2011

(54) TARGET SUBSTANCE DETECTION METHOD AND TARGET SUBSTANCE DETECTION KIT

(75) Inventors: Mie Okano, Yokohama (JP); Junta Yamamichi, Cambridge, MA (US)

(73) Assignee: Canon Kabushiki Kaisha, Tokyo (JP)

( * ) Notice: Subject to any disclaimer, the term of this patent is extended or adjusted under 35 U.S.C. 154(b) by 448 days.

(21) Appl. No.: 12/122,061

(22) Filed: May 16, 2008

(65) Prior Publication Data

US 2008/0227218 A1    Sep. 18, 2008

Related U.S. Application Data

(63) Continuation-in-part of application No. 12/039,390, filed on Feb. 28, 2008, now abandoned.

(30) Foreign Application Priority Data

Mar. 16, 2007    (JP) ............................... 2007-069052

(51) Int. Cl.
*G01N 33/553* (2006.01)
(52) U.S. Cl. .................... 436/525; 385/12; 385/129; 385/130; 422/82.11; 435/287.2; 435/288.7; 435/808; 436/164; 436/805
(58) Field of Classification Search ........................ None
See application file for complete search history.

(56) References Cited

U.S. PATENT DOCUMENTS 6,331,276 B1 * 12/2001 Takei et al. .............. 422/82.09
2005/0176049 A1    8/2005 Watanabe

FOREIGN PATENT DOCUMENTS

JP    3452837 B2    7/2003
JP    2005-257667 A    9/2005

* cited by examiner

*Primary Examiner*—Christopher L Chin
(74) *Attorney, Agent, or Firm*—Fitzpatrick, Cella, Harper & Scinto (57) ABSTRACT

A target substance detection method for detecting a target substance in a specimen, comprises the steps of contacting with a specimen a target substance detecting element comprised of a base, a metal structure and a first capturing body for capturing a target substance; contacting with the target substance detecting element a labeling material comprised of a labeling substance and a second capturing body for capturing a target substance; and acquiring an absorption spectrum (A) of the target substance detecting element contacted with the specimen and the labeling material, wherein the employed labeling substance is a substance that a slope of a tangent of an absorption spectrum (C) of the labeling substance at a peak wavelength ($\lambda_z$) of an absorption spectrum (B) of the target substance detecting element is larger than zero.

4 Claims, 7 Drawing Sheets

TARGET SUBSTANCE DETECTION METHOD AND TARGET SUBSTANCE DETECTION KIT

CROSS-REFERENCE TO RELATED APPLICATIONS

This is a continuation-in-part application of the U.S. patent application Ser. No. 12/039,390 filed on Feb. 28, 2008.

BACKGROUND OF THE INVENTION

1. Field of the Invention

The present invention relates to a target substance detection method and a target substance detection kit for detecting a target substance in a specimen.

2. Description of the Related Art

A measuring method in which metal micro-particles are fixed on a base surface and a substance near the metal micro-particles is detected using localized surface plasmon resonance induced there is known. When light is incident onto metal micro-particles, such as gold and silver, a characteristic resonance spectrum appears by the localized surface plasmon resonance. It is known that its resonance wavelength is dependent on a dielectric constant of a medium near the metal micro-particles. As the dielectric constant becomes large, absorbance of a resonance peak becomes large and shifts to a long wavelength region. For example, Okamoto et al. have proposed a system using a gold colloid with a diameter of about 20 nm (Japanese patent No. 3452837 specification). This system is adapted to detect a refractive index of a certain medium by a distance which is about a diameter of a metal micro-particle fixed to the base, and consequently, it is possible to detect absorption and deposition of a substance (antigen in an antigen-antibody reaction) on a metal micro-particle surface.

In addition, Watanabe et al. have proposed a sensor technique which can measure an interaction concerning materials with high precision (Japanese Patent Application Laid-Open No. 2005-257667). Here, an example of labeling DNA with a dielectric crystal to be used for plasmon resonance is disclosed. Here, double stranded DNA constructed of DNA changed beforehand so as to become single stranded DNA when a target substance bonds together, and complementary DNA labeled with the dielectric crystal are immobilized on a detection surface where plasmon resonance occurs. When a target substance bonds with DNA on the detection surface, a distance between the dielectric and base changes and the target substance is detected using this change.

Nevertheless, detection methods which used the localized surface plasmon resonance and have been invented until now, have not been sufficient in detection sensitivity in an affinity assay such as an immunoassay using specificity of an antigen-antibody reaction or the like, and hence, further enhancement in the sensitivity has been desired.

SUMMARY OF THE INVENTION

The present invention solves the problem in the background art mentioned above, and aims at providing a target substance detection method and a target substance detection kit which can enhance the detection sensitivity in detection of a target substance using the localized surface plasmon resonance.

The present invention is directed to a target substance detection method for detecting a target substance in a specimen, comprising the steps of contacting with a specimen a target substance detecting element, including at least a base, a metal structure which exists on a surface of the base and a first capturing body for capturing a target substance which exists on a surface of the metal structure; after the contacting step or simultaneously with the contacting step, contacting with the target substance detecting element a labeling material comprised of a labeling substance and a second capturing body for capturing a target substance; and acquiring an absorption spectrum (A) of the target substance detecting element contacted with the specimen and the labeling material, wherein the employed labeling substance is a substance that aslope of a tangent of an absorption spectrum (C) of the labeling substance in a liquid at a peak wavelength ($\lambda_z$) of an absorption spectrum (B) of the target substance detecting element, being contacted with the specimen and the second capturing body, in the liquid is larger than zero. The labeling substance can be one of an inorganic oxide and an organic substance.

The present invention is directed to a target substance detection kit for detecting a target substance in a specimen, comprising at least: a target substance detecting element including a base, a metal structure which exists on a surface of the base and a first capturing body for capturing a target substance which exists on a surface of the metal structure; and a labeling material which contains at least a second capturing body for capturing a target substance labeled with a labeling substance, wherein the labeling substance is a substance that an slope of a tangent of an absorption spectrum (C) of the labeling substance in a liquid at a peak wavelength ($\lambda_z$) of an absorption spectrum (B) of the target substance detecting element, being contacted with the specimen and the second capturing body, in the liquid is larger than zero. The labeling substance can be one of an inorganic oxide and an organic substance.

In addition, the present invention is a target substance detection kit for detecting a target substance in a specimen, including at least: a target substance detecting element including a base, a metal structure which exists on a surface of the base, and a first capturing body for capturing a target substance which exists on a surface of the metal structure; and a labeling material which contains at least a second capturing body for capturing a target substance labeled with a labeling substance, characterized in that an absorption spectrum of the labeling substance in a liquid can be approximated by a straight line whose slope is larger than zero when linear approximation is performed within the range of +50 nm from a peak wavelength of an absorption spectrum which the target substance detecting element in a state of capturing the target substance has in the liquid, or that an absorption spectrum of the labeling substance in a gas can be approximated by a straight line whose slope is larger than zero when linear approximation is performed within the range of +200 nm from a peak wavelength of an absorption spectrum which the target substance detecting element in a state of capturing the target substance has in the gas.

In addition, the present invention is a target substance detection method for detecting a target substance in a specimen, including: acquiring a transmission spectrum by radiating light on the target substance detecting element after contacting a target substance detecting element including at least a base, a metal structure which exists on a surface of the base, and a first capturing body which exists on a surface of the metal structure, with a labeling material which contains at least a second capturing body for capturing a target substance labeled with a labeling substance, and the target substance; and detecting presence of the target substance in the specimen, or a concentration of the target substance in the specimen by the acquired transmission spectrum, characterized in that an absorption spectrum of the labeling substance in a liquid can be approximated by a straight line whose slope is larger than zero when linear approximation is performed within the range of +50 nm from a peak wavelength of an absorption spectrum which the target substance detecting element in a state of capturing the target substance has in the liquid; or that an absorption spectrum of the labeling substance in a gas can be approximated by a straight line whose slope is larger than zero when linear approximation is performed within the range of +200 nm from a peak wavelength of an absorption spectrum which the target substance detecting element in a state of capturing the target substance has in the gas.

Here, it is suitable that the labeling substance is one of an inorganic oxide and an organic substance.

Further features of the present invention will become apparent from the following description of exemplary embodiments with reference to the attached drawings.

DESCRIPTION OF THE EMBODIMENTS

Hereafter, embodiments for implementing the present invention will be described. In addition, the present invention is not limitedly interpreted by the following embodiments and examples. For example, by modifying materials, composition conditions, reaction conditions and the like of the following embodiments and examples freely in a range of what those skilled in the art can understand, the present invention can be achieved.

(Target Substance Detection Method)

In addition, a first aspect of the present invention is a target substance detection method for detecting a target substance in a specimen. A target substance detection method has the following steps (1) to (3).

(1) A first step of contacting a target substance detecting element, including at least a base, a metal structure which exists on a surface of the base, and a first capturing body for capturing a target substance which exists on a surface of the metal structure, with a specimen (2) A second step of being a step being performed after the first step or simultaneously with the first step, and contacting a labeling material, which includes a labeling substance and a second capturing body for capturing a target substance, with the target substance detecting element (3) A third step of acquiring an absorption spectrum (A) of the target substance detecting element after the second step The labeling substance employed in the method is such that a slope of a tangent of an absorption spectrum (C) of the labeling substance in a liquid at a peak wavelength ($\lambda_z$) of an absorption spectrum (B) of the target substance detecting element, being contacted with the specimen and the second capturing body, in the liquid is larger than zero.

Hereafter, each step will be described.

About Step (1)

In the step (1), a specimen is contacted with a target substance detecting element, including at least a base, a metal structure which exists on a surface of the base, and a first capturing body for capturing a target substance which exists on a surface of the metal structure. When contacting a target substance detecting element and a specimen, the specimen may be contacted with the target substance detecting element, or the target substance detecting element may be dipped in the specimen.

Hereafter, target substance detecting element will be described.

Figure 1A:
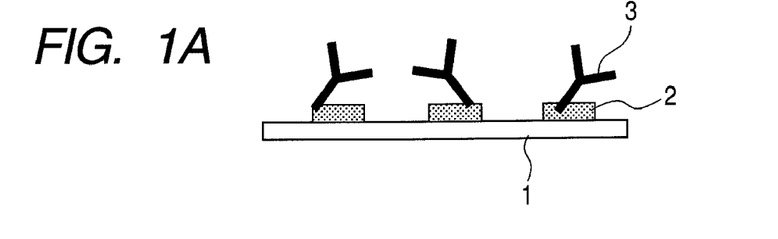
FIGS. 1A and 1B are schematic diagrams illustrating an example of a target substance detection kit of the present invention.

An example of the target substance detecting element is illustrated in FIG. 1A. The target substance detecting element has at least a base 1, a metal structure 2 which exists on a surface of the base 1, and a first capturing body 3 for capturing a target substance which exists on a surface of the metal structure 2. In addition, although not illustrated, a specimen and a buffer solution are supplied to the detecting element. For example, a container for holding a specimen and the like and a flow path may be connected to the specimen.

Next, respective parts (base, metal structure, and capturing body) which construct the target substance detecting element will be described.

(Base)

So long as having a function of supporting the metal structure 2, the base 1 can be constructed of any materials. As materials of the base, for example, inorganic materials, such as a resin, glass, and silicon, which are generally used as materials of the base can be used. In addition, when performing detection using transmitted light, it is preferable that the base is made of a material whose transmittance is large. In that case, a transmittance is preferably within a range between 80% and 100%. In addition, as the light for measuring the transmittance, light with a wavelength of 400 to 600 nm can be used, for example. As examples of a preferable base in an aspect of the transmittance, a glass base, a quartz base, resin bases, such as polycarbonate and polystyrene base, and a base with ITO (Indium-Tin Oxide) and the like are cited. In addition, the base may be constructed of one layer or may be constructed of a plurality of layers. When the base is constructed of the plurality of layers, a part which fixes a metal structure on a top surface may have a functional group with high affinity with metal, such as an amino group or a thiol group, or may be a membrane, which strengthens adhesive strength during the base and the metal structure, such as a membrane which is made of chromium, titanium or the like. In addition, parts other than the part which constructs the metal structure may be nonspecific adsorption preventing films.

In addition, when the surface of the base 1 is not limited to be smooth, it is general that the metal structure exists on an approximately smooth base surface as a state that the metal structure which generates localized surface plasmon resonance exists on the surface of the base. Here, it is defined that "approximately smooth" means that surface roughness is 5 nm or less.

(Metal Structure)

The metal structure exists on the surface of the base 1, and generates the localized surface plasmon resonance. As a material of the metal structure, any metal among gold, silver, copper, platinum, and aluminum, or an alloy containing at least one kind of those elements can be used suitably. What are cited as examples of a form of the metal structure are a form which has not many sides called a globular form (particle shape) and an approximately globular form, a form which is constructed by cutting off partially a globular form, or an approximately globular form, various polyhedral forms, such as a cylinder, a multiple pillar, a cone, a pyramid, a ring form with thickness, parallel crosses and a quad-square with thickness and the like. In addition, when describing and paying attention to a production method, several examples among the metal structures of the present invention each can be called a metal pattern. Furthermore, when producing a metal structure on a base using various film-forming methods, it is hard to measure its size with a grain size measuring apparatus. Suitable size of the metal structure in such a case is as follows. First, thickness (mean thickness in a direction perpendicular to a base surface) is preferably within a range between 10 nm and 100 nm. In addition, size (a maximum distance between two arbitrary points in the metal structure in a plane parallel to a metal structure formed surface of the base) is preferably within a range between 10 nm and 1450 nm, and more preferably between 50 nm and 450 nm.

An interval between two metal structures 2 (minimal length between adjacent metal structures) is preferably within a range between 50 nm and 2 μm, and more preferably between 150 nm and 1 μm. When the interval is too narrow, the distribution and the intensity of the spatial electric field are influenced by the interaction of the metal structures due to surface plasmon and in consequence, sensor sensitivity may drop. In addition, when the interval is too large, signal intensity may become weak because of low density of metal structures, and when the signal intensity becomes weak, a special optical system may become necessary in order to enhance sensitivity.

(Target Substance and Capturing Body)

A capturing body recognizes and captures a target substance, and the capturing body and a target substance form a complex. In addition, it is needless to say that the capturing body here includes both of the first capturing body in step (1), and the second capturing body in step (2).

As such a capturing body, for example, the followings can be cited as typical ones.

(i) Those recognizing a form, size and the like of the target substance using three dimensional structure of a high molecular compound.

(ii) Those recognizing the target substance using a hydrogen bond, a coordinate bond, an electrostatic interaction, a canal field and the like.

(iii) Those recognizing the target substance using complexly some of structure, bonds, operations and the like of (i) and (ii).

In this way, "capture" as used in the present invention and this specification is a concept of including widely general material recognition using various interactions. The target substance captured is not limited to a biological material, and size is also not limited. In addition, the target substance may be not only a comparatively small one such as an ion or a molecule, but also an aggregate of molecules, a cell or the like.

What are cited as combinations of such a target substance and a capturing body are antigen-antibody, enzyme-substrate, DNA-DNA, DNA-RNA, RNA-RNA, amino acid-antibody, sugar-lectin, vitamin-antibody, and quasi-antibody-antigen and the like. Here, description of "A-B" as a target substance and a capturing body shows combination of A and B. Hence, it is assumed that it shows both of a case that a target substance is A and a capturing body is B, and a case that a target substance is B and a capturing body is A. In addition, a capturing body is suitably selected according to a target substance, and when selecting the capturing body, it is possible to refer to various textbooks and documents regarding biochemistry, chemistry of complex and the like. In addition, it is also possible to obtain a capturing body by producing an antibody corresponding to a specific antigen (target substance) using a mouse, a rat, a rabbit or the like. Furthermore, it is not necessary that a measuring object of the target substance detecting element of the present invention be a target substance on which the capturing body directly acts, but the measuring object may be what is measured indirectly.

In addition, FIGS. 4A to 4F illustrate changes of an absorption spectrum of the target substance detecting element by performing step (1). "a" of FIG. 4D denotes the absorption spectrum of the target substance detecting element (FIG. 4A) contacted with a liquid before performing step (1), and "b" of FIG. 4D denotes the absorption spectrum of the target substance detecting element (FIG. 4B) contacted with the liquid after performing step (1). When the target substance detecting element 7 captures the target substance 6, a dielectric constant (refractive index) near the metal structure 2 changes, and the absorption spectrum changes from "a" of FIG. 4D to "b" of FIG. 4D.

Here, the absorption spectrum is obtained by irradiating an object and acquiring transmitted light from the object. Hence, the absorption spectrum of the target substance detecting element is a transmission spectrum which is obtained by light being radiated on the target substance detecting element and being transmitted from the target substance detecting element. In addition, although the radiated light changes with a material, a form, and size of the metal structure, it is suitable that the radiated light is within the range of 200 to 1500 nm.

About Step (2)

In step (2), a second capturing body for capturing a target substance is contacted with the target substance detecting element having been contacted with the specimen at step (1). In addition, although this is described above with supposing a case that step (2) is performed after step (1), step (1) and step (2) may be performed simultaneously. When the steps are performed simultaneously, the case that the second capturing body captures the target substance which the first capturing body captured, and the case that the first capturing body further captures the target substance captured by the second capturing body occur simultaneously.

Here, it is suitable that areas where the first capturing body which the target substance detecting element has, and the second capturing body which the labeling material has capture the target substance are different. That is, it is suitable the area where the first capturing body recognizes and captures the target substance, and the area where the second capturing body recognizes and captures the target substance are different. Hence, when being captured, the target substance becomes in a state of being sandwiched and captured by the first capturing body and the second capturing body. In addition, as long as the areas where the target substance is recognized are different, the first capturing body and the second capturing body may be the same type, or may be different types.

Next, the labeling substance will be described.

Figure 1B:
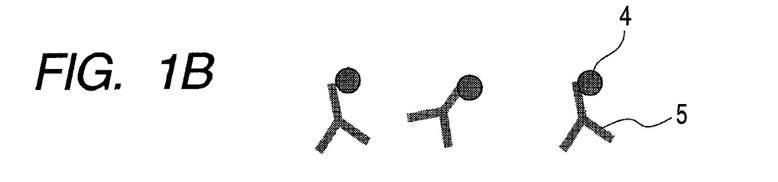

An example of the labeling material is illustrated in FIG. 1B.

A labeling material 8 is constructed of a labeling substance 4 and a second capturing body 5 for capturing a target substance.

As the labeling material, a labeling substance is used in which an slope of a tangent of an absorption spectrum (C) of the labeling substance in a liquid at a peak wavelength ($\lambda_z$) of an absorption spectrum (B) of the target substance detecting element, being contacted with the specimen and the second capturing body, in the liquid is larger than zero.

Specifically, the labeling material is a labeling substance which has the following optical properties.

Figure 4A:
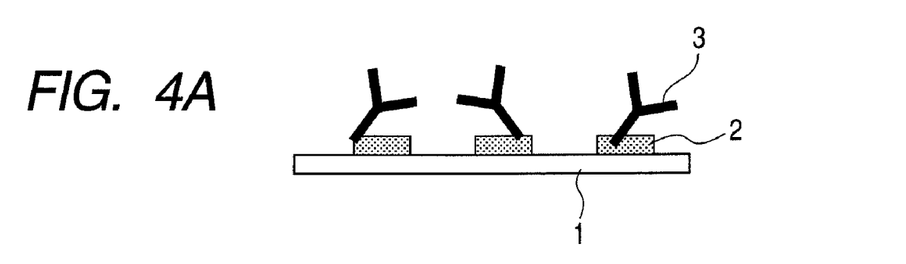
FIGS. 4A, 4B, 4C, 4D, 4E and 4F are schematic diagrams illustrating an example of a target substance detection method of the present invention and its result.
Figure 4B:
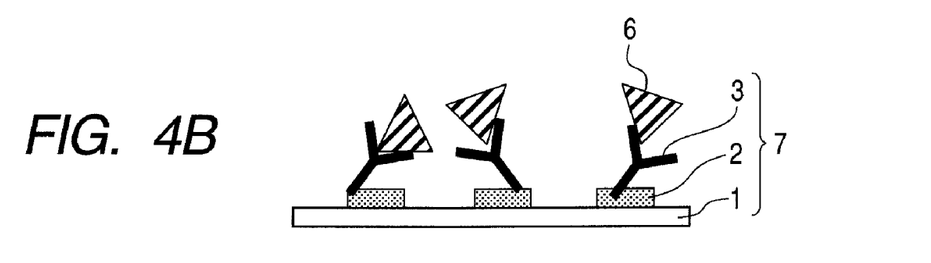
Figure 4C:
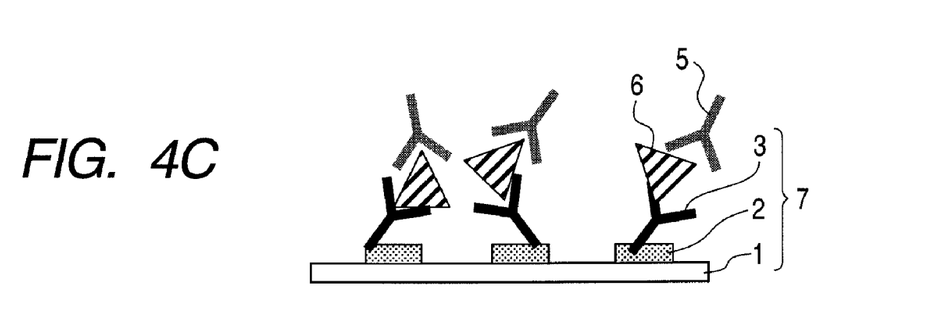

As shown in FIG. 4C, when step (2) is performed simultaneously with step (1) or after step (1), the second capturing body 5 and the first capturing body 3 capture the target substance 6 in sandwich structure. An absorption spectrum in the liquid of the target substance detecting element in the state illustrated in FIG. 4C becomes an absorption spectrum c in FIG. 4D. A peak wavelength of the absorption spectrum c is $\lambda_z$, and a refractive index changes into $\lambda_y < \lambda_z$ by the second capturing body being fixed near the metal structure.

Figure 4D:
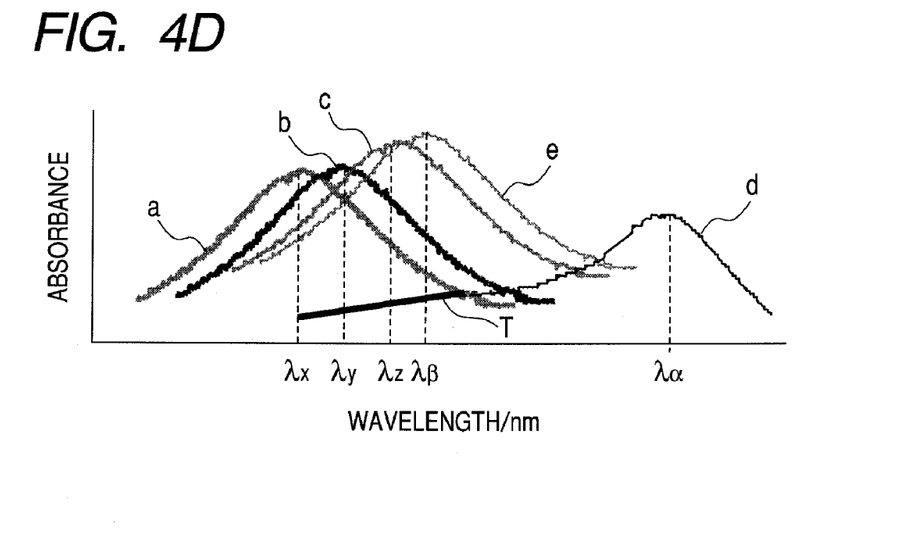
Figure 4E:
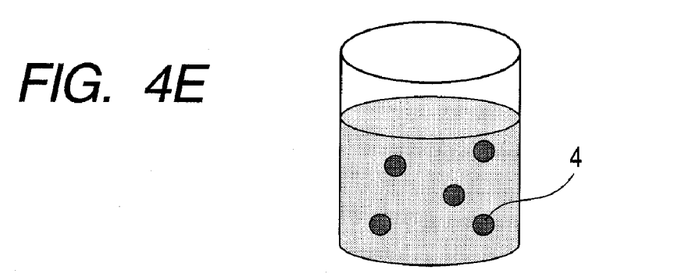

The labeling substance has a slope of a tangent t at a peak wavelength ($\lambda_z$) of the absorption spectrum c of the target substance detecting element in FIG. 4C in the liquid in the absorption spectrum (d in FIG. 4D) in the case of existing in the liquid illustrated in FIG. 4E is larger than zero. In addition, the suitable labeling substance has a wavelength longer than the peak wavelength ($\lambda_z$) of the absorption spectrum c of the target substance detecting element in FIG. 4C.

Figure 4F:
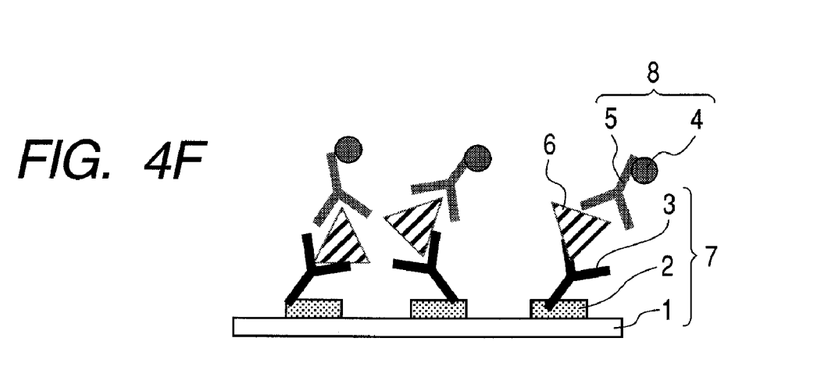

When the labeling substance has the optical properties mentioned above, an absorption spectrum e of the target substance detecting element (target substance detecting element obtained at step (2)), contacted with the liquid after being contacted with the labeling material 8 and the specimen as illustrated in FIG. 4F, in the liquid shifts greatly in a long wavelength region. That is, a peak wavelength $\lambda_\beta$ of the absorption spectrum e of the target substance detecting element, obtained at step (2), in the liquid becomes further long wavelength. This is because the absorption spectrum e becomes an addition of a spectrum derived from the labeling substance and a spectrum caused by the localized surface plasmon resonance of the metal structure which the target substance detecting element has, when the labeling material captures the target substance.

About a phenomenon that the spectrum derived from the labeling substance and the spectrum caused by the localized surface plasmon resonance of the metal structure which the target substance detecting element has are added together, it is possible to prove it simply by performing a simulation. For example, a case of preparing a material, which has absorption at nearly 800 nm, as a labeling substance, and dissolving the material in a phosphate buffer will be described. An absorption spectrum at the time of applying a labeling substance solution on the target substance detecting element which has the absorption at nearly 600 nm has an absorption peak at nearly 800 nm derived from the labeling substance, and an absorption peak at nearly 600 nm derived from the target substance detecting element. Thus, the absorption spectrum e becomes an addition of the absorption spectrum of labeling substance in the phosphate buffer and the absorption spectrum of the target substance detecting element in the phosphate buffer. In addition, it is also possible to verify that a form of the absorption spectrum derived from the labeling substance does not change. Thus, it can be possible to estimate an advantageous effect of spectrum addition, by measuring the absorption spectrum which the labeling substance in the solution has.

Figure 3:
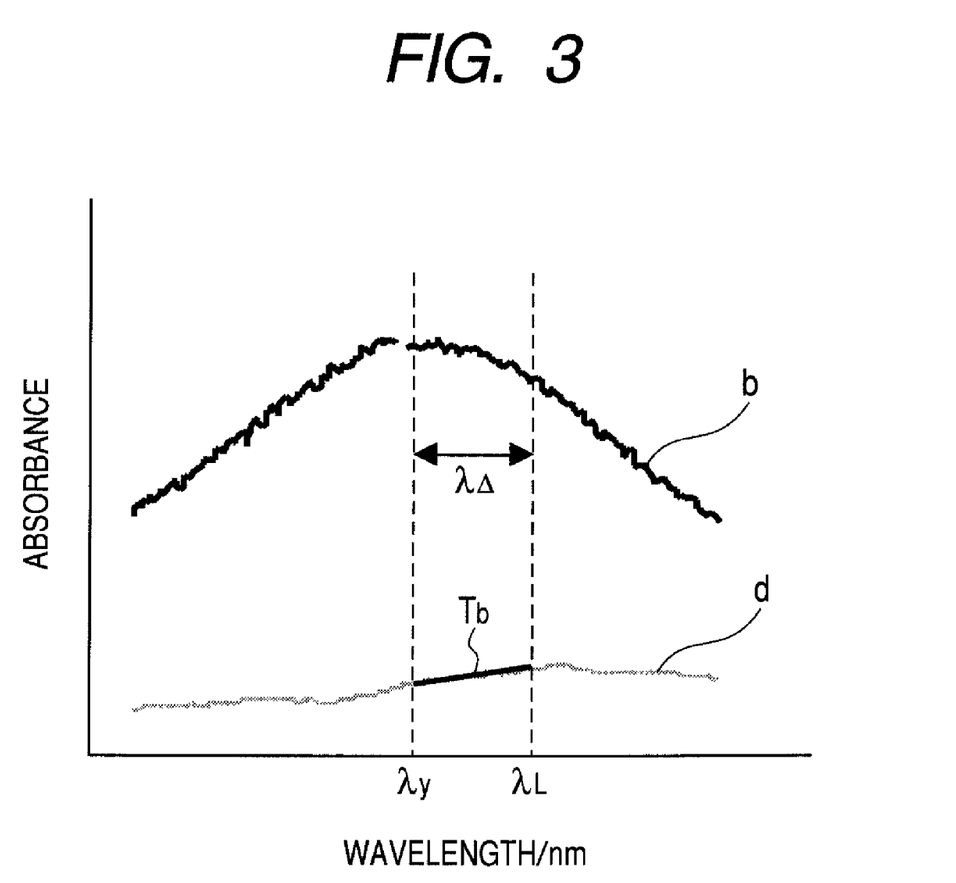
FIG. 3 is a schematic diagram illustrating an example of relationship between the absorption spectrum of the labeling material contained in the target substance detection kit of the present invention, and the absorption spectrum of the target substance detecting element in a state of capturing the target substance.

Here, as illustrated in FIG. 3, it is a high probability that the absorption spectrum of the labeling substance in the liquid can be approximated by a straight line $T_b$ whose slope is larger than zero when linear approximation is performed within a range $\lambda_A$ from a wavelength ($\lambda_y$), expressing a peak wavelength of absorbance spectrum, to a wavelength $\lambda_L$ which is larger by +50 nm in the absorption spectrum (b in FIG. 4D) which the target substance detecting element (FIG. 4B) in a state of capturing the target substance has in the liquid, or that an absorption spectrum of the labeling substance in a gas can be approximated by a straight line whose slope is larger than zero when linear approximation is performed within the range of +200 nm from a wavelength expressing peak wavelength of absorption spectrum which the target substance detecting element in a state of capturing the target substance has in the gas. Here, it is suitable that slope of an approximately straight line is $1 \times 10^{-6}$ or more. A range of the linear approximation is set with reference to experimental values. Although a change of an absorption spectrum depends on an amount of a target substance, or a type of a metal structure, when the target substance and the second capturing body were contacted with the target substance detecting element on some condition, the change of the spectrum in the air was about 4 times as large as that in a solvent. In addition, although depending on an amount of a target substance, or a type of a metal structure, a change of a spectrum in a solution is within the range of 0 nm to 50 nm. With reference to the above experimental values, it is defined that the range $\lambda_A$ of the linear approximation is +50 nm in a solution and +200 nm in the air. Here, as a method of the linear approximation, it is possible to use a least square method.

In addition, since it is sufficient to use a labeling substance which has the optical properties in step (2), when it turns out that the optical characteristic of the labeling substance fulfills the conditions, it is not necessary to acquire spectra of the absorption spectrum (c in FIG. 4D) of the target substance detecting element in the state of FIG. 4C, and the absorption spectrum (d in FIG. 4D) of the labeling substance in the state of FIG. 4E also in any of steps (1) to (3).

So long as it has the optical characteristic, mentioned above, as a material of a labeling substance, what kind of material may be used. As a material which constructs a labeling substance, it is possible to use, for example, one of an inorganic oxide and an organic substance. More specifically, it is possible to use polymer particles which are constructed of polystyrene or a polystyrene derivative, soda lime glass or the like. In addition, it is also sufficient to use dye-content polymer particles which are polymer particles containing dye. Nevertheless, it is suitable that the labeling substance is a material which does not react with the metal structure.

About Step (3)

Step (3) acquires an absorption spectrum (A) of the target substance detecting element (FIG. 4F) obtained at step (2). Here, the absorption spectrum (A) is the absorption spectrum e in FIG. 4D.

As the labeling materials bond with the target substances at step (2), an influence of a peak derived from the labeling substances becomes large. As a result, a shift amount to become large, and, detection sensitivity of detecting a target substance improves.

In addition, when acquiring beforehand an absorption spectrum of a target substance detecting element contacted with a solution, which contains a target substance in known concentration, and a labeling material, and acquiring relationship between the concentration of the target substance and the shift amount of the peak wavelength of absorption spectrum of the target substance detecting element, it is possible to determine the concentration of the target substance in a specimen. In addition, it is also possible to take a reference when detecting the target substance. In such a case, it is possible to acquire the absorption spectrum ("a" in FIG. 4D) of the target substance detecting element before contacting with the target substance to make the absorption spectrum into a reference.

Next, a second aspect of the present invention will be described.

The second aspect of the present invention is a target substance detection kit.

The target substance detection kit for detecting a target substance in a specimen according to the present invention has at least the following components.

(Target Substance Detecting Element)
Base
Metal structure existing on a surface of the base
First capturing body existing on a surface of the metal structure In addition, a production method of a target substance detecting element and a labeling material will be described hereinafter.

(Production Method of Target Substance Detecting Element)

Figure 2A:
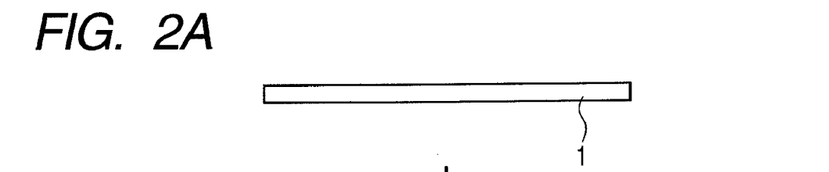
FIGS. 2A, 2B and 2C are schematic diagrams illustrating an example of a production method of a target substance detecting element of the present invention.
Figure 2B:
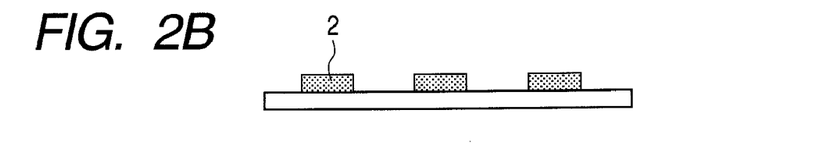
Figure 2C:
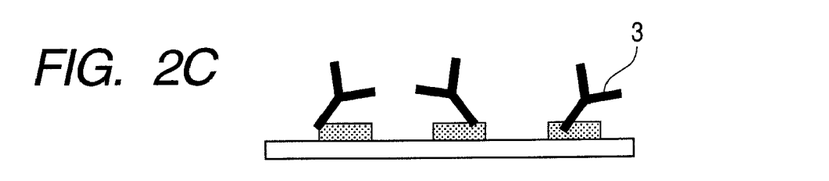

An example of a production method of the target substance detecting element related to the present invention will be illustrated in FIGS. 2A to 2C. In the example illustrated in FIGS. 2A to 2C, the metal structure 2 is formed on the base 1, and the first capturing body 3 is bonded on the metal structure 2. At the time of forming the metal structure 2, metal particles may be arranged in a predetermined position on the base 1, and a metallic film pattern may be formed on the base 1. When the metallic film pattern is formed on the base 1, patterning may be performed after forming the metallic film on the base 1, or the metallic film pattern may be formed directly using an ink jet method, a dispensing method, a micro contact printing method or the like.

In addition, when bonding the capturing body 3 on the metal structure 2, various well-known chemical reactions can be used. For example, a covalent bond, an ionic bond, absorption and the like are cited.

In the bonding system, it is also sufficient to react directly the capturing body having a reaction group, which can act directly, on the metal structure to make the capturing body bonded, or it is satisfactory to react a crosslinking material, which can act directly, on the metal structure to react the capturing body with the crosslinking material. When the metal structure contains one of gold, silver and copper, it is possible to directly fix the capturing body which has a thiol group, an amino group or the like. In addition, it is also fixable by reacting a crosslinking material, such as a silane coupling agent which has a thiol group, an amino group or the like with the metal structure, and further making the capturing body bonded with this crosslinking material.

In the absorption system, what is necessary is just to select a combination which has adequate affinity among combinations of material of the capturing body and material of the metal structure. In addition, it is also possible to form a surface which has adequate affinity and to fix the capturing body, by modifying a surface of the metal structure.

(Production Method of Labeling Material)

Next, a production method of a labeling material will be described. At the time of bonding the second capturing body and labeling substance, various publicly-known chemical reactions can be used. For example, a covalent bond, an ionic bond, absorption and the like are cited.

In the bonding system, it is also sufficient to react directly the labeling substance having a reaction group, which can act directly on the capturing body to make them bonded, or it is satisfactory to react a crosslinking material, which can act directly on the labeling substance, and to react the capturing body with the crosslinking material to make them bonded. For example, it is also possible to bond a capturing body which has an amino group with a labeling substance which has a carboxyl group by amino coupling process.

In the absorption system, what is necessary is just to select a combination which has adequate affinity among combinations of the labeling substance and material of the capturing body. In addition, it is also possible to form a surface which has adequate affinity and to fix the capturing body, by modifying a surface of the labeling substance.

EXAMPLE

The present invention will be further specifically described with example below.

Example 1

This example is an example which performs patterning of a gold structure on a base using an electron-beam lithography system, bonds bovine serum albumin with the gold structure to produce a target substance detecting element, and detects an anti-bovine serum albumin antibody using this. As a labeling material, an anti-rabbit IgG(Fc) antibody labeled with a bead made from polystyrene is used.

(Production of Target Substance Detecting Element)

Patterning of Metal Structure on Quartz Base

Figure 5:
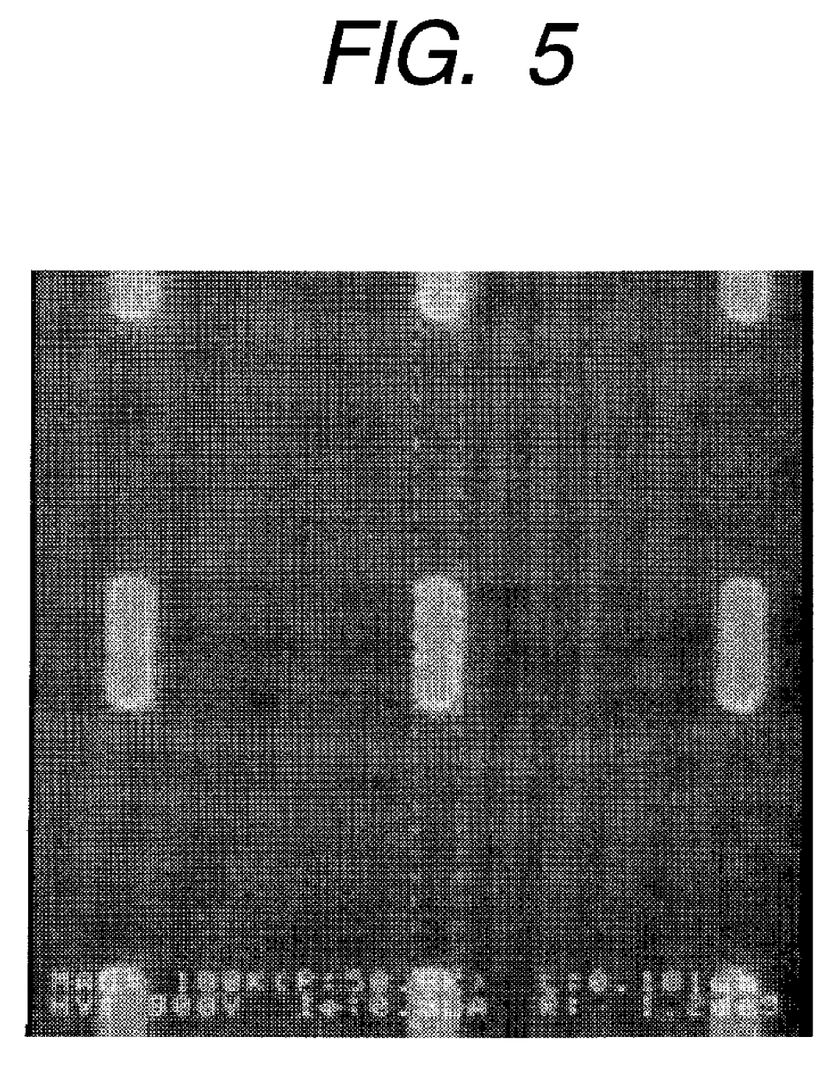
FIG. 5 is an example of a SEM image of a target substance detecting element of the present invention on the way of production.

First, a metal structure is produced by forming a gold thin film with 25 nm of film thickness on a quartz base with 625 µm of thickness, and performing patterning this into a predetermined pattern using an electron-beam lithography system. A planar form of the metal structure (300 nm×100 nm) is verified with a scanning electron microscope (SEM) image (its example is illustrated in FIG. 5). Hereinafter, the base with the metal structure, which is obtained in this way, is expressed as a base A.

Introduction of First Capturing Body

By dissolving bovine serum albumin in a phosphate buffer, immersing the base A in a solution, and leaving them at room temperature under a shaking condition, the bovine serum albumin (first capturing body) is made to be fixed to the metal structure surface physically. The target substance detecting element is produced according to the above step.

(Absorption Spectrum Measurement of Target Substance Detecting Element)

By contacting the phosphate buffer, including an anti-bovine serum albumin antibody (target substance) at a concentration of $1\times10^{-5}$ g/mL, with the target substance detecting element which is obtained, the target substance is bonded with the target substance detecting element.

(Production Method of Labeling Material)

Next, a selection method of the labeling substance which constructs a labeling material will be described. First procedure is to contact a sample to the target substance detecting element in the state of FIG. 4A to make it a target substance detecting element in the state of FIG. 4B. Then, further procedure is to contact the anti-rabbit IgG(Fc) antibody, which is the second capturing body in the same amount as an amount used later as a second capturing body for capturing a target substance of a labeling material, with the target substance detecting element contacted with the sample to obtain the target substance detecting element in the state of being illustrated in FIG. 4C. Then, the procedure is to acquire a peak wavelength ($\lambda_z$) of the absorption spectrum (B) (c in FIG. 4D) in the phosphating solution in the state of being illustrates in FIG. 4C.

In addition, the procedure is to obtain the absorption spectrum (C) (d in FIG. 4D) in the phosphate buffer, including the labeling substance (state of FIG. 4E). Here, as the labeling substance, polystyrene particles with the carboxyl group on surfaces of the particles are used. Then, the procedure is to acquire a tangent at the $\lambda_z$ in the absorption spectrum (C) of the labeling substance obtained, and to verify that a slope of this tangent is larger than zero.

Next, the procedure is to dissolve an anti-rabbit IgG(Fc) antibody (second capturing body for capturing a target substance) in the phosphate buffer, to add the polystyrene particles with a carboxyl group to the solution to mix them at room temperature under shaking condition, and to make the antibodies and the polystyrene particles with a carboxyl group covalently bonded or physically adsorbed.

It is also sufficient to clean the obtained labeling material with the phosphate buffer after the reaction to measure the absorption spectrum in the phosphate buffer.

In addition, since the labeling substance has the following optical characteristics in many cases, it is sufficient to select the labeling substance by the following methods.

That is, a labeling substance has an absorption spectrum which can be approximated in a straight line with a slope larger than zero when linear approximation is performed within the range of the wavelength ($\lambda_y$), at which a peak wavelength of the absorption spectrum (b in FIG. 4D) of the target substance detecting element (FIG. 4B), with which the target substance is bonded, in the phosphate buffer is indicated, to +50 nm.

Furthermore, when using the air instead of the phosphate buffer, the labeling substance has an absorption spectrum which can be approximated in a straight line with a slope larger than zero when linear approximation is performed within the range of the wavelength, at which a peak wavelength of the absorption spectrum of the target substance detecting element, with which the target substance is bonded, in the air is indicated, to +200 nm.

Specifically, the selection method of a labeling substance will be described hereinafter.

In the selection method of a labeling material mentioned above, the peak wavelength of the absorption spectrum $\lambda_y$ is determined by obtaining the absorption spectrum (b in FIG. 4D) of the target substance detecting element in the phosphating solution in the state of FIG. 4B of being bonded with the target substance.

Next, the procedure is to obtain the absorption spectrum (d in FIG. 4D) in the phosphate buffer, including the labeling substance (state of FIG. 4E). Here, as the labeling substance, polystyrene particles with the carboxyl group on surfaces of the particles are used.

Then, as illustrated in FIG. 3, the procedure is to verify that it is possible to approximate an absorption spectrum with a straight line whose slope is larger than zero when performing linear approximation of the absorption spectrum of the labeling substance within the range of $\lambda_y$ to +50 nm, and to select the labeling substance.

In addition, it is also sufficient to calculate a wavelength $\lambda_\gamma$ at which a peak wavelength of the absorption spectrum of the target substance detecting element in the air in the state of FIG. 4B which is bonded with the target substance is indicated, to verify that it is possible to approximate an absorption spectrum with a straight line whose slope is larger than zero when performing linear approximation of the absorption spectrum of the labeling substance within the range of $\lambda_y$ to +200 nm, and to select the labeling substance.

Furthermore, as a method of linearly approximating an absorption spectrum, it is possible to use a least square method.

The target substance detecting element and the labeling material which are prepared by the above procedure are produced.

It is also possible to preserve the obtained labeling material in a predetermined solution.

In addition, the target substance detecting element and the labeling material are made to be a target substance detection kit.

(Target Substance Detection Method)

Figure 6:
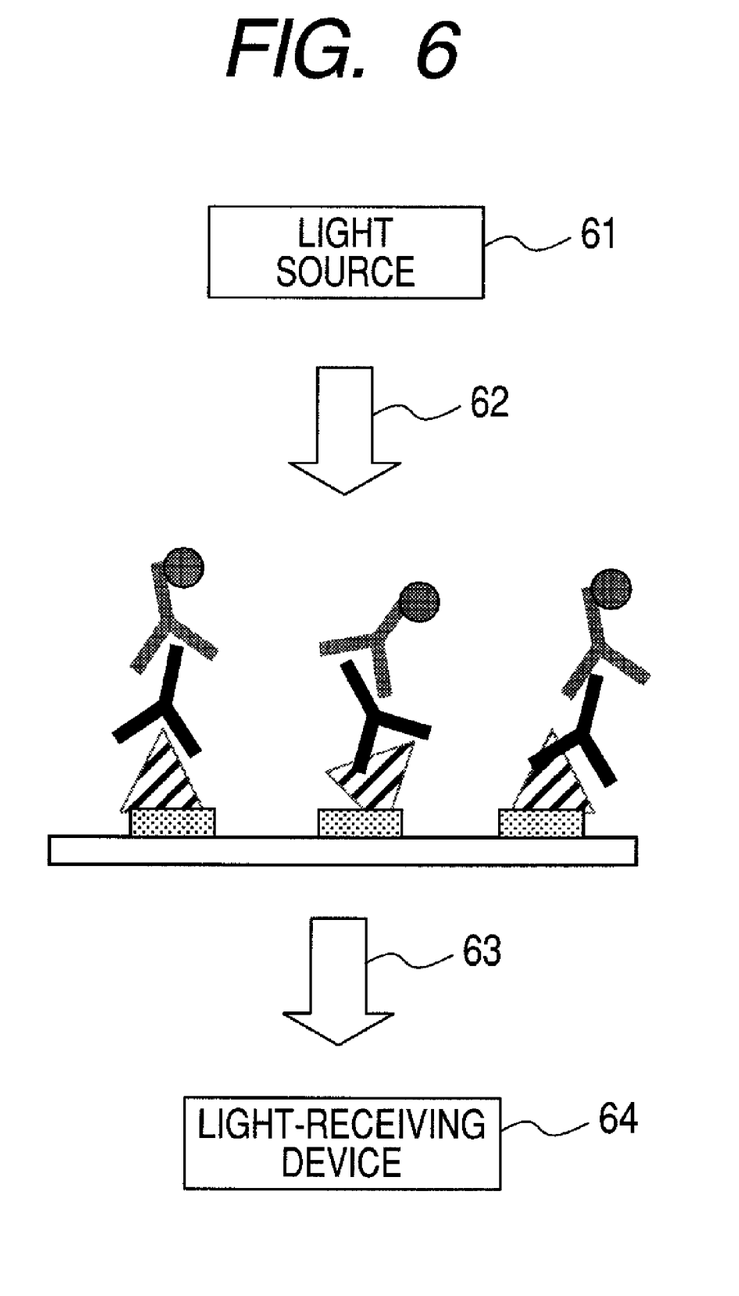
FIG. 6 is a schematic diagram for describing the target substance detection method in a first example.

Next, detection is performed using the target substance detection kit. FIG. 6 is a diagram schematically illustrating a detection concept of this example. A light source 61 at the time of detection is arranged in a position from which measurement light 62 may be radiated on a target substance detecting element as schematically illustrated in FIG. 6. A light-receiving device 64 is arranged in a position in which it is possible to detect characteristics of the measurement light 63 which transmits the target substance detecting element. In addition, besides this, a spectral detection device not illustrated may be provided in the light-receiving device. Furthermore, it is suitable that an arithmetic apparatus which arithmetically operates a detected characteristic change, a display apparatus which displays a detection consequence and the like are provided. In addition, the display apparatus and arithmetic apparatus may be united, or they may be separate bodies.

First, by contacting the target substance detecting element and phosphate buffer, and arranging the target substance detecting element, light source, and light-receiving device in positional relation illustrated in FIG. 6, a spectrum of the target substance detecting element in the phosphate buffer is detected. The following procedure is to supply a sample which is the phosphate solution including an anti-bovine serum albumin antibody as a target substance to react the target substance and the first capturing body which the target substance detecting element has. After that, the procedure is to add again a phosphate buffer and to remove materials not bonded. Then, the procedure adds the labeling material dissolved in the phosphate buffer to react them, and thereafter, to add the phosphate buffer to remove the labeling material not bonded. The subsequent procedure is to arrange again the target substance detecting element, light source, and light-receiving device in the positional relation illustrated in FIG. 6, and to detect the absorption spectrum (A) of the target substance detecting element in which the target substance and labeling material bond. The spectral change before and after supply of a sample and the labeling material is derived from a change of a plasmon resonance state of the metal structure, and means that an antigen-antibody reaction occurs on a surface of the target substance detecting element, the target substance is captured by the first capturing body, and the labeling material bonds with the target substance. Therefore, presence of the target substance and its concentration in the sample can be detected by detecting a spectral change.

In addition, here, the relationship between the spectral change and the target substance concentration is acquired beforehand using standard samples with a plurality of known concentrations. When obtaining a calibration curve on the basis of this relationship and obtaining a function between the spectral change and the concentration, it is possible to obtain a target substance concentration from the spectral change at the time of actual measurement using this function. In addition, although described as the spectral change here, this spectral change may be a change of the spectral peak at the wavelength with a maximum (peak wavelength of the spectrum), or a change of peak shape, such as half-value width of a waveform of a spectral peak, may be used. Furthermore, it is sufficient to use a change of light intensity in one or a plurality of wavelength points.

Figure 7A:
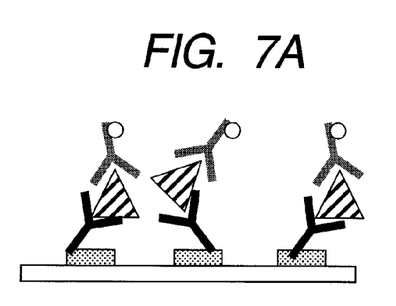
FIGS. 7A, 7B, 7C and 7D are conceptual drawings for illustrating difference between advantageous effects of the present invention and a conventional example.
Figure 7B:
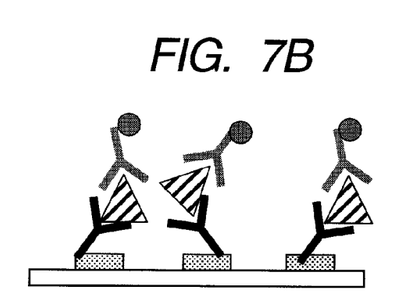
Figure 7C:
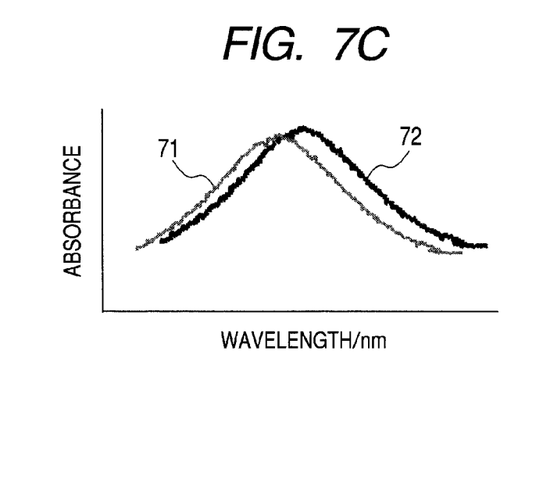
Figure 7D:
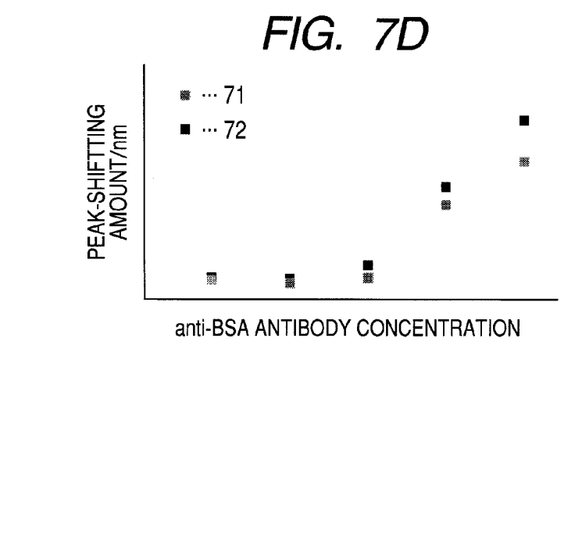

Furthermore, in the above example, in comparison with a case that the labeling material included in the target substance detection kit in the present invention is not used, detection sensitivity increases. Such an advantageous effect is schematically illustrated in FIGS. 7A to 7D. That is, in FIGS. 7A to 7D, a change of the absorption spectrum of the target substance detecting element in a case 72 that the labeling substance of the labeling material which is constructed of the labeling substance and the second capturing body has the absorption spectrum characteristics (in FIG. 7B), and a case 71 that the labeling substance does not have the absorption spectrum characteristics (in FIG. 7A) is illustrated. In FIG. 7D, a vertical axis is the extent of shift of the peak wavelength (nm), and a horizontal axis is the anti-BSA antibody concentration. Because of these, according to the present invention, it is possible to increase the extent of shift of the peak wavelength in a case that a target substance in the same concentration exists in a specimen, by using the characteristics of the absorption spectrum of the labeling material.

As described above, sensitivity enhancement can be achieved by using the target substance detection method and target substance detection kit according to the present invention.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2007-069052, filed Mar. 16, 2007, which is hereby incorporated by reference herein in its entirety.

What is claimed is:

1. A target substance detection method for detecting a target substance in a specimen, comprising the steps of:

contacting with a specimen a target substance detecting element, including at least a base, a metal structure which exists on a surface of the base and a first capturing body for capturing a target substance which exists on a surface of the metal structure;

after the contacting step or simultaneously with the contacting step, contacting with the target substance detecting element a labeling material comprised of a labeling substance and a second capturing body for capturing a target substance; and acquiring an absorption spectrum (A) of the target substance detecting element contacted with the specimen and the labeling material, wherein the employed labeling substance is a substance that a slope of a tangent of an absorption spectrum (C) of the labeling substance in a liquid at a peak wavelength ($\lambda_z$) of an absorption spectrum (B) of the target substance detecting element, being contacted with the specimen and the second capturing body, in the liquid is larger than zero.

2. The target substance detection method according to claim 1, wherein the labeling substance is one of an inorganic oxide and an organic substance.

3. A target substance detection kit for detecting a target substance in a specimen, comprising at least:

a target substance detecting element including a base, a metal structure which exists on a surface of the base and a first capturing body for capturing a target substance which exists on a surface of the metal structure; and a labeling material which contains at least a second capturing body for capturing a target substance labeled with a labeling substance, wherein the labeling substance is a substance that a slope of a tangent of an absorption spectrum (C) of the labeling substance in a liquid at a peak wavelength ($\lambda_z$) of an absorption spectrum (B) of the target substance detecting element, being contacted with the specimen and the second capturing body, in the liquid is larger than zero.

4. The target substance detection kit according to claim 3, wherein the labeling substance is one of an inorganic oxide and an organic substance.

* * * * *